United States Patent
Likhotvorik

(10) Patent No.: US 6,887,999 B1
(45) Date of Patent: May 3, 2005

(54) PREPARATION OF DIHYDROCODEINE FROM CODEINE

(75) Inventor: Igor Likhotvorik, Culver, IN (US)

(73) Assignee: Acura Pharmaceuticals, Inc., Palatine, IL (US)

( * ) Notice: Subject to any disclaimer, the term of this patent is extended or adjusted under 35 U.S.C. 154(b) by 0 days.

(21) Appl. No.: 10/851,527

(22) Filed: May 21, 2004

(51) Int. Cl.7 .................... C07D 489/02; C07D 489/00
(52) U.S. Cl. ........................................ 546/44; 546/43
(58) Field of Search ................................. 546/44, 43

(56) References Cited

U.S. PATENT DOCUMENTS 3,830,819 A   8/1974   Grew
3,953,883 A   4/1976   Grew

OTHER PUBLICATIONS

Black, Howard T. et al., Synthetic Communications, "A Rapid, Nearly Quantitative conversion of Codeine to Hydrocodone," V. 30, No. 17, pp. 3195–3201, (2000), by Marcel Dekker, Inc.

Rapoport, Henry et al., The Journal of Organic Chemistry, "The Preparation of Some Dihydro Ketones in the Morphine Series by Oppenauer Oxidation," V. 15, No. 4, pp. 1103–1107, (1950), Published by The Williams & Wilkins Company, Baltimore, MD, USA.

Van Duin, Constant Frederik et al., Journal of the Chemical Society, "The Morphine Group, Part III. The Constitution of Neopine," pp. 903–908, (1926), London.

Wieland, Heinrich et al., Justus Liebig's Annalen der Chermie, "Einige Bemerkungen zur Konstituition des Morphins," V. 433, pp. 267–271, (1923), Verlag Chemie, GmbH., Leipzig u. Berlin, Printed in Germany.

Primary Examiner—Charanjit S. Aulakh
(74) Attorney, Agent, or Firm—Morgan, Lewis & Bockius LLP

(57) ABSTRACT

A process for the preparation of dihydrocodeine by hydrogenating codeine or a salt thereof in aqueous solution in the presence of a catalytic metal and deactivating agent that decreases impurities formation.

17 Claims, No Drawings

PREPARATION OF DIHYDROCODEINE FROM CODEINE

FIELD OF THE INVENTION

The present invention relates to a process for the preparation of dihydrocodeine from codeine.

BACKGROUND OF THE INVENTION

Dihydrocodeine is a widely used semisynthetic narcotic analgesic possessing also useful antitussive properties. It is also an important intermediate for the synthesis of other opioid analgesics, e.g. hydrocodone.

Dihydrocodeine has been prepared by hydrogenation of neopine (J. Chem Soc. (1926), 903). However, since neopine is one of the least available morphine alkaloids this method has little practical value.

Another method of dihydrocodeine preparation is described in U.S. Pat. Nos. 3,830,819 and 3,853,883 as hydrogenation of hydrocodone. Hydrocodone itself is usually produced from codeine or thebaine by multi-step synthetic transformations. As compared to the synthesis from codeine, which is discussed below, this adds additional steps to the process, leading to dihydrocodeine production that is not cost-effective.

Hydrogenation of codeine in the presence of palladium catalysts is a straightforward method of dihydrocodeine preparation (Ann. (1923), 433, 269, J. Org. Chem. (1950), 15, 1103; Synth. Commun. (2000), 30, 3195). Usually hydrogenation requires large amounts of organic solvents, leading to increased health risk for the manufacturing personnel, and also posing environmental hazard. These disadvantages of organic solvents may be eliminated by using water as a safe, so-called "green" solvent. However, in aqueous solutions (J. Org. Chem. (1950), 15, 1105), hydrogenation is complicated by uncontrollable side reactions, because metal catalysts used for the hydrogenation induce isomerization of codeine to hydrocodone and also promote cleavage of the 4,5-epoxymorphinane ring of the molecule to form dihydrothebainone. Removal of these impurities from dihydrocodeine to the levels acceptable for the pharmaceutical use is a very tedious process, resulting in substantial yield loss.

In view of above, there is a need for an efficient, economical, safe and environmentally friendly process for the production of dihydrocodeine.

SUMMARY OF THE INVENTION

The process in accordance with the invention is a process for the preparation of dihydrocodeine by hydrogenating codeine or a salt thereof in aqueous solution in the presence of a catalytic metal and deactivating agent that decreases impurities formation.

One embodiment of the present invention includes a process for the production of dihydrocodeine, which includes reacting codeine or a salt thereof in an aqueous solution with hydrogen in the presence of at least one catalytic metal selected from group VIII of the Periodic Table of Elements and at least one deactivating agent that decreases impurities formation.

Another embodiment of the present invention includes a process for the production of dihydrocodeine, which includes reacting codeine or a salt thereof in an aqueous solution with hydrogen in the presence of at least one catalytic metal selected from the group consisting of nickel, palladium, rhodium, ruthenium, platinum and at least one base that decreases impurities formation.

Another embodiment of the invention includes a process for the production of dihydrocodeine, which includes reacting codeine or a salt thereof in an aqueous solution with hydrogen in the presence of at least one a catalytic metal selected from group VIII of the Periodic Table of Elements and at least one inorganic base that decreases impurities formation.

DETAILED DESCRIPTION OF THE INVENTION

Advantageously in one embodiment of the process of the present invention, hydrogenation of codeine or a salt thereof (e.g., phosphate) in aqueous solution in the presence of a catalytic metal and deactivating agent results in production of dihydrocodeine with desirable purity and yield.

One embodiment of the process of the present invention requires a catalytic metal to provide an active surface for the addition of the hydrogen to the double bond of codeine resulting in dihydrocodeine formation. Suitable metals for use herein can be selected from group VIII of the Periodic Table of Elements. In one embodiment, suitable metals can include, but are not limited to, nickel, palladium, rhodium, ruthenium, platinum, and combinations thereof. The catalysts have been described in the literature and are available commercially.

Suitable catalytic metals may be supported and/or unsupported metal catalysts generally used for heterogeneous hydrogenation. In one embodiment, a catalytic metal can be supported on carbon, aluminum oxide and/or barium sulfate. In one embodiment, a catalytic metal can be present in amounts of about 0.01 to about 1.0 mol % on a support. In one embodiment, a catalytic metal can be present in amounts of about 0.05 to about 0.25 mol % on a support. In one embodiment, a catalytic metal can be present on a support at less than or equal to about 10% by weight, preferably less than about 5% by weight.

One embodiment of the process of the invention is carried out in the presence of a deactivating agent. Any suitable agent capable of minimizing isomerization side reactions of codeine bonded to the surface of the catalytic metal may be used as a deactivating agent.

In one embodiment of the process of the present invention, suitable deactivating agents for use herein include, but are not limited to inorganic bases. Preferred inorganic bases include, but are not limited to, ammonium hydroxide, lithium hydroxide, potassium hydroxide, sodium hydroxide, cesium hydroxide, ammonium bicarbonate, lithium carbonate, potassium carbonate, potassium phosphate, sodium carbonate, sodium phosphate, cesium carbonate and combinations thereof.

In another embodiment of the process of the present invention, suitable deactivating agents for use herein include, but are not limited to, organic bases. In one embodiment, the organic base includes a nitrogenous base. Preferred organic bases include, but are not limited to codeine, dihydrocodeine and combinations thereof.

In yet another embodiment of the process of the present invention, suitable deactivating agents for use herein include, but are not limited to, combinations of inorganic bases and organic nitrogenous bases.

In one embodiment, one or more organic and/or inorganic bases can be present in amounts sufficient to maintain pH of the aqueous solution from about 5 to about 11. In one embodiment, an organic and/or inorganic base is present in amounts sufficient to maintain pH of the aqueous solution from about 5 to about 10. Preferably an inorganic and/or organic base is present in amounts sufficient to maintain pH of the aqueous solution from about 5 to about 9. Most preferably, the base is present in amounts sufficient to maintain pH of the aqueous solution from about 6 to about 8.

In one embodiment, one or more of the above-described catalytic metals can also be used as a deactivating agent. In one embodiment, the deactivating agent can be one or more of nickel, palladium, rhodium, ruthenium, platinum, and combinations thereof. Accordingly, in some embodiments of the present invention, a catalyst metal and a deactivating agent can be the same. In a preferred embodiment of the invention, platinum is used as both the catalytic metal and deactivating agent.

In a most preferred embodiment of the invention, platinum is used as both the catalytic metal and deactivating agent in the presence of yet another deactivating agent selected from the group of inorganic bases and organic bases mentioned hereinbefore, and combinations thereof.

In the present invention, the hydrogenation process is generally carried out at ambient temperatures. In one embodiment, the present invention can be carried out at about 20° C. to about 35° C. In one embodiment, the present invention can be carried out at about 25° C. to about 30° C. A suitable reaction hydrogen pressure is conveniently from about 10 to about 50 psig. In one embodiment, the reaction hydrogen pressure can be from about 17 to about 37 psig. In one embodiment, the reaction hydrogen pressure can be from about 12 to about 17 psig.

The completion of hydrogenation can be determined by any suitable analytical technique such as thin layer chromatography (TLC) or high performance liquid chromatography (HPLC).

Dihydrocodeine can be isolated from the reaction mixture using techniques that are well known to those skilled in the art. In one embodiment, the isolated dihydrocodeine can contain less than about 1.0%, preferably less than about 0.5%, hydrocodone and/or less than about 1.0%, preferably less than about 0.5%, dihydrothebainone. In one embodiment of the invention, the purity of the isolated dihydrocodeine is equal to or greater than 98.0% and in one embodiment the purity of the isolated dihydrocodeine is equal to or greater than 99.0%.

The following examples are given to illustrate the present invention. It should be understood, however, that the invention is not to be limited to the specific conditions or details described in these examples. Throughout the specification, any and all references to a publicly available document, including but not limited to a U.S. patent, are specifically incorporated by reference.

EXAMPLE 1

Hydrogenation of codeine phosphate at different pH, 14% codeine concentration in solution (Table 1, Experiments No. 1, 3, 4, 5, 8, 10–14, 17):

without deactivating agent on a palladium on carbon catalyst (Experiment No. 1);

in the presence of platinum as deactivating agent with a platinum on carbon catalyst (Experiment No. 3);

in the presence of sodium hydroxide as deactivating agent (Experiments No. 4 (palladium on carbon catalyst), 8 (palladium on carbon catalyst), 10 (rhodium on carbon catalyst), 11 (ruthenium on carbon catalyst), 12 (palladium on aluminum oxide catalyst), and 13 (palladium on carbon catalyst));

in the presence of ammonium hydroxide as deactivating agent with a palladium on carbon catalyst (Experiment No. 5);

in the presence of potassium hydroxide as deactivating agent with a palladium on carbon catalyst (Experiment No. 17);

in the presence of platinum and sodium hydroxide as deactivating agents with a platinum on carbon catalyst (Experiment No. 14).

Codeine phosphate was dissolved in water, and pH was adjusted by adding aqueous solution of inorganic base until pH of the solution reached the level indicated in the Table 1 for experiments No. 4, 5, 8, 10–14, and 17. For experiments No. 1 and 3 no pH adjustments were done. Solution was agitated under 10–50 psig of hydrogen pressure at 25–30° C. in the presence of about 0.05–0.25 mol % palladium on carbon, palladium on barium sulfate, palladium on alumina, rhodium on carbon, ruthenium on carbon, platinum on carbon as indicated in the Table 1, until codeine conversion was completed. The mixture was analyzed by HPLC to determine dihydrocodeine content, [DHC %] and also contents of two major impurities: hydrocodone [H %] and dihydrothebainone [DHT %] in the product of hydrogenation (Table 1).

EXAMPLE 2

Hydrogenation of codeine acetate at different pH without deactivating agent (Table 1, Experiment No.2), and in the presence of codeine and dihydrocodeine, that is formed during hydrogenation, as deactivating agents (Table 1, Experiment No.6).

Glacial acetic acid was added to a suspension of codeine (5 g) in water (50 mL) until codeine dissolved and pH of the solution reached the level indicated in the Table 1. Solution was agitated under 12–17 psig of hydrogen pressure at 25–30° C. in the presence of 5% palladium on barium sulfate (0.1–1.0 g) until codeine conversion was completed. The mixture was analyzed by HPLC to determine dihydrocodeine content, [DHC %] and also contents of two major impurities: hydrocodone [H %] and dihydrothebainone [DHT %] in the product of hydrogenation (Table 1).

EXAMPLE 3

Hydrogenation of codeine hydrochloride, codeine acetate, codeine sulfate, codeine phosphate at pH 7.3–7.5 and codeine at pH 9.8 in diluted aqueous solution, 0.8% codeine concentration in solution, in the presence of codeine and dihydrocodeine, that is formed during hydrogenation, as deactivating agents (Table 1, Experiments No. 7, 9, 15, 16, 18).

Codeine was dissolved in water and pH was adjusted by adding aqueous solution of hydrochloric acid (Experiment 7), acetic acid (Experiment 9), sulfuric acid (Experiment 15), or phosphoric acid (Experiment 16) until pH of the solution reached the level indicated in the Table 1. Solution was agitated under 17–37 psig of hydrogen pressure at 25–30° C. in the presence of about 0.25 mol % palladium on carbon until codeine conversion was completed. The mixture was analyzed by HPLC to determine dihydrocodeine content, [DHC %] and also contents of two major impurities: hydrocodone [H %] and dihydrothebainone [DHT %] in the product of hydrogenation (Table 1).

TABLE 1

| Exp. No. | Deactivating agent | pH | Catalyst | DHC % | H % | DHT % |
|---|---|---|---|---|---|---|
| 1 | none | 4.1 | 5% Pd/C | 87.6 | 6.9 | 5.5 |
| 2 | none | 4.1 | 5% Pd/BaSO$_4$ | 87.9 | 8.2 | 3.8 |
| 3 | Pt | 4.2 | 5% Pt/C | 98.2 | 0.7 | 0.5 |
| 4 | NaOH | 6.2 | 5% Pd/C | 95.5 | 1.7 | 2.8 |
| 5 | NH$_4$OH | 6.5 | 5% Pd/C | 92.8 | 2.0 | 3.2 |
| 6 | Codeine/ dihydrocodeine | 7.3 | 5% Pd/BaSO$_4$ | 97.0 | 2.2 | 0.8 |
| 7 | Codeine/ dihydrocodeine | 7.3 | 5% Pd/C | 97.8 | 0.8 | 1.3 |
| 8 | NaOH | 7.4 | 5% Pd/C | 95.8 | 1.4 | 2.8 |
| 9 | Codeine/ dihydrocodeine | 7.4 | 5% Pd/C | 97.6 | 0.9 | 1.4 |
| 10 | NaOH | 7.4 | 5% Rh/C | 96.4 | 0.8 | 2.8 |
| 11 | NaOH | 7.4 | 5% Ru/C | 94.8 | 0.7 | 4.5 |
| 12 | NaOH | 7.5 | 5% Pd/Al$_2$O$_3$ | 95.7 | 1.2 | 3.1 |
| 13 | NaOH | 7.5 | 5% Pd/C | 96.7 | 1.0 | 1.8 |
| 14 | Pt, NaOH | 7.5 | 5% Pt/C | 99.5 | 0.0 | 0.5 |
| 15 | Codeine/ dihydrocodeine | 7.5 | 5% Pd/C | 97.8 | 1.3 | 0.9 |
| 16 | Codeine/ dihydrocodeine | 7.5 | 5% Pd/C | 98.1 | 0.6 | 1.3 |
| 17 | KOH | 7.7 | 5% Pd/C | 95.4 | 1.5 | 2.3 |
| 18 | Codeine/ dihydrocodeine | 9.8 | 5% Pd/C | 97.3 | 1.4 | 1.3 |

The results in Table 1 show that in the absence of deactivating agent (Experiments 1,2) hydrogenation of codeine is accompanied by excessive side reactions achieving the highest levels of two major impurities, both hydrocodone and dihydrothebainone. The results in Table 1 also show that significant yield and desired purity of dihydrocodeine may be achieved when hydrogenation is performed in the presence of deactivating agents or combinations thereof.

While the invention has been described in detail and with reference to specific embodiments thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents. Further, each and every reference disclosed herein is hereby incorporated by reference.

What is claimed is:

1. A process for the production of dihydrocodeine, which comprises reacting codeine or a salt thereof in an aqueous solution with hydrogen in the presence of
   (i) at least one catalytic metal selected from group VIII of the Periodic Table of Elements; and
   (ii) at least one deactivating agent that decreases impurities formation.

2. The process of claim 1, wherein the catalytic metal is selected from the group consisting of nickel, palladium, rhodium, ruthenium, platinum, and combinations thereof.

3. The process of claim 1, wherein deactivating agent is selected from the group consisting of an inorganic base, organic nitrogenous base, platinum and combinations thereof.

4. The process of claim 3, wherein platinum is used as both the catalytic metal and deactivating agent.

5. The process of claim 3, wherein the inorganic base is selected from the group consisting of ammonium hydroxide, lithium hydroxide, potassium hydroxide, sodium hydroxide, cesium hydroxide, ammonium bicarbonate, lithium carbonate, potassium carbonate, potassium phosphate, sodium carbonate, sodium phosphate, cesium carbonate and combinations thereof.

6. The process of claim 3, wherein the organic nitrogenous base is selected from the group consisting of codeine, dihydrocodeine and combinations thereof.

7. The process of claim 3, wherein organic base or a combination of organic base and inorganic base is present in amounts sufficient to maintain pH of the aqueous solution from about 5 to about 11.

8. The process of claim 3, wherein the inorganic base is present in amounts sufficient to maintain pH of the aqueous solution from about 5 to about 10.

9. The process of claim 3, wherein the inorganic base, organic base or a combination thereof is present in amounts sufficient to maintain pH of the aqueous solution from about 5 to about 9.

10. The process of claim 9, wherein the inorganic base, organic base or a combination thereof is present in the amounts sufficient to maintain pH of the aqueous solution from about 6 to about 8.

11. A process for the production of dihydrocodeine, which comprises reacting codeine or a salt thereof in an aqueous solution with hydrogen in the presence of
    (i) at least one a catalytic metal selected from group VIII of the Periodic Table of Elements; and
    (ii) at least one inorganic base that decreases impurities formation.

12. The process of claim 11, wherein the inorganic base comprises sodium hydroxide.

13. The process of claim 11, wherein the inorganic base is present in amounts sufficient to maintain pH of the aqueous solution from about 5 to about 10.

14. A process for the production of dihydrocodeine, which comprises reacting codeine or a salt thereof in an aqueous solution with hydrogen in the presence of
    (i) at least one catalytic metal selected from the group consisting of nickel, palladium, rhodium, ruthenium, platinum; and
    (ii) at least one base that decreases impurities formation.

15. The process of claim 14, wherein the base comprises an inorganic base.

16. The process of claim 15, wherein the inorganic base comprises sodium hydroxide.

17. The process of claim 15, wherein the inorganic base is present in amounts sufficient to maintain pH of the aqueous solution from about 5 to about 10.

* * * * *